(12) United States Patent
Miller et al.

(10) Patent No.: US 12,396,785 B2
(45) Date of Patent: Aug. 26, 2025

(54) SYSTEM OF MEDICAL DEVICES AND METHOD FOR PERICARDIAL PUNCTURE

(71) Applicant: Boston Scientific Medical Device Limited, Ballybrit (IE)

(72) Inventors: Brock Miller, Toronto (CA); Matthew Gravett, Milton (CA); Kai-Lon Fok, Mississauga (CA); Rund Abou-Marie, Mississauga (CA)

(73) Assignee: Boston Scientific Medical Device Limited, Galway (IE)

( * ) Notice: Subject to any disclaimer, the term of this patent is extended or adjusted under 35 U.S.C. 154(b) by 250 days.

(21) Appl. No.: 17/393,499

(22) Filed: Aug. 4, 2021

(65) Prior Publication Data
US 2022/0047324 A1    Feb. 17, 2022

Related U.S. Application Data

(60) Provisional application No. 63/064,435, filed on Aug. 12, 2020.

(51) Int. Cl.
| | | |
|---|---|---|
| *A61B 18/14* | (2006.01) | |
| *A61B 18/12* | (2006.01) | |
| *A61B 18/00* | (2006.01) | |

(52) U.S. Cl.
CPC ...... *A61B 18/1477* (2013.01); *A61B 18/1206* (2013.01); *A61B 2018/00083* (2013.01); *A61B 2018/00351* (2013.01); *A61B 2018/00755* (2013.01)

(58) Field of Classification Search
CPC ............ A61B 17/3478; A61B 18/1206; A61B 18/1477; A61B 18/1487; A61B 2017/00247; A61B 2018/00083; A61B 2018/00351; A61B 2018/00363; A61B 2018/00601; A61B 2018/00755; A61B 2018/00875; A61B 2090/065

See application file for complete search history.

(56) References Cited

U.S. PATENT DOCUMENTS

| | | |
|---|---|---|
| 175,254 A | 3/1876 | Oberly |
| 827,626 A | 7/1906 | Gillet |
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |

(Continued)

*Primary Examiner* — Michael F Peffley
(74) *Attorney, Agent, or Firm* — Nelson Mullins Riley & Scarborough LLP

(57) ABSTRACT

A system for pericardial puncture includes a medical device having an elongate shaft extending between a proximal end and a distal end, and having a distally facing electrode at the distal end of the shaft. An impedance meter is electrically connectable with the electrode for measuring an impedance associated with the electrode. A display is provided for displaying an indication of a position of the electrode. The indication of the position is based on of the impedance.

14 Claims, 4 Drawing Sheets

(56) References Cited

U.S. PATENT DOCUMENTS

| | | | |
|---|---|---|---|
| 4,244,362 A | 1/1981 | Anderson | |
| 4,401,124 A | 8/1983 | Guess et al. | |
| 4,639,252 A | 1/1987 | Kelly et al. | |
| 4,641,649 A | 2/1987 | Walinsky et al. | |
| 4,669,467 A | 6/1987 | Willett et al. | |
| 4,682,596 A | 7/1987 | Bales et al. | |
| 4,790,311 A | 12/1988 | Ruiz | |
| 4,790,809 A | 12/1988 | Kuntz | |
| 4,793,350 A | 12/1988 | Mar et al. | |
| 4,807,620 A | 2/1989 | Strul et al. | |
| 4,832,048 A | 5/1989 | Cohen | |
| 4,840,622 A | 6/1989 | Hardy | |
| 4,863,441 A | 9/1989 | Lindsay et al. | |
| 4,884,567 A | 12/1989 | Elliott et al. | |
| 4,892,104 A | 1/1990 | Ito et al. | |
| 4,896,671 A | 1/1990 | Cunningham et al. | |
| 4,928,693 A | 5/1990 | Goodin et al. | |
| 4,936,281 A | 6/1990 | Stasz | |
| 4,960,410 A | 10/1990 | Pinchuk | |
| 4,977,897 A | 12/1990 | Hurwitz | |
| 4,998,933 A * | 3/1991 | Eggers | A61B 18/1492 606/41 |
| 5,006,119 A | 4/1991 | Acker et al. | |
| 5,019,076 A | 5/1991 | Yamanashi et al. | |
| 5,047,026 A | 9/1991 | Rydell | |
| 5,081,997 A | 1/1992 | Bosley et al. | |
| 5,098,431 A | 3/1992 | Rydell | |
| 5,112,048 A | 5/1992 | Kienle | |
| 5,154,724 A | 10/1992 | Andrews | |
| 5,201,756 A | 4/1993 | Horzewski et al. | |
| 5,209,741 A | 5/1993 | Spaeth | |
| 5,211,183 A | 5/1993 | Wilson | |
| 5,221,256 A | 6/1993 | Mahurkar | |
| 5,230,349 A | 7/1993 | Langberg | |
| 5,281,216 A | 1/1994 | Klicek | |
| 5,300,068 A | 4/1994 | Rosar et al. | |
| 5,300,069 A | 4/1994 | Hunsberger et al. | |
| 5,314,418 A | 5/1994 | Takano et al. | |
| 5,318,525 A | 6/1994 | West et al. | |
| 5,327,905 A | 7/1994 | Avitall | |
| 5,364,393 A | 11/1994 | Auth et al. | |
| 5,372,596 A | 12/1994 | Klicek et al. | |
| 5,380,304 A | 1/1995 | Parker | |
| 5,397,304 A | 3/1995 | Truckai | |
| 5,403,338 A | 4/1995 | Milo | |
| 5,423,809 A | 6/1995 | Klicek | |
| 5,425,382 A | 6/1995 | Golden et al. | |
| 5,490,859 A | 2/1996 | Mische et al. | |
| 5,497,774 A | 3/1996 | Swartz et al. | |
| 5,507,751 A | 4/1996 | Goode et al. | |
| 5,509,411 A | 4/1996 | Littmann et al. | |
| 5,514,131 A * | 5/1996 | Edwards | A61N 1/403 606/41 |
| 5,540,681 A | 7/1996 | Strul et al. | |
| 5,545,200 A | 8/1996 | West et al. | |
| 5,555,618 A | 9/1996 | Winkler | |
| 5,571,088 A | 11/1996 | Lennox et al. | |
| 5,575,766 A | 11/1996 | Swartz et al. | |
| 5,575,772 A | 11/1996 | Lennox | |
| 5,599,347 A | 2/1997 | Hart et al. | |
| 5,605,162 A | 2/1997 | Mirzaee et al. | |
| 5,617,878 A | 4/1997 | Taheri | |
| 5,622,169 A | 4/1997 | Golden et al. | |
| 5,624,430 A | 4/1997 | Eton et al. | |
| 5,667,488 A | 9/1997 | Lundquist et al. | |
| 5,673,695 A | 10/1997 | McGee et al. | |
| 5,674,208 A | 10/1997 | Berg et al. | |
| 5,683,366 A | 11/1997 | Eggers et al. | |
| 5,720,744 A | 2/1998 | Eggleston et al. | |
| 5,741,249 A | 4/1998 | Moss et al. | |
| 5,766,135 A | 6/1998 | Terwilliger | |
| 5,779,688 A | 7/1998 | Imran et al. | |
| 5,810,764 A | 9/1998 | Eggers et al. | |
| 5,814,028 A | 9/1998 | Swartz et al. | |
| 5,830,214 A | 11/1998 | Flom et al. | |
| 5,836,875 A | 11/1998 | Webster, Jr. | |
| 5,849,011 A | 12/1998 | Jones et al. | |
| 5,851,210 A | 12/1998 | Torossian | |
| 5,885,227 A | 3/1999 | Finlayson | |
| 5,888,201 A | 3/1999 | Stinson et al. | |
| 5,893,848 A | 4/1999 | Negus et al. | |
| 5,893,885 A | 4/1999 | Webster, Jr. | |
| 5,904,679 A | 5/1999 | Clayman | |
| 5,916,210 A | 6/1999 | Winston | |
| 5,921,957 A | 7/1999 | Killion et al. | |
| 5,931,818 A | 8/1999 | Werp et al. | |
| 5,944,023 A | 8/1999 | Johnson et al. | |
| 5,951,482 A | 9/1999 | Winston et al. | |
| 5,957,842 A | 9/1999 | Littmann et al. | |
| 5,964,757 A | 10/1999 | Ponzi | |
| 5,967,976 A | 10/1999 | Larsen et al. | |
| 5,989,276 A | 11/1999 | Houser et al. | |
| 6,007,555 A | 12/1999 | Devine | |
| 6,009,877 A | 1/2000 | Edwards | |
| 6,013,072 A | 1/2000 | Winston et al. | |
| 6,017,340 A | 1/2000 | Cassidy et al. | |
| 6,018,676 A | 1/2000 | Davis et al. | |
| 6,030,380 A | 2/2000 | Auth et al. | |
| 6,032,674 A | 3/2000 | Eggers et al. | |
| 6,048,340 A * | 4/2000 | Miyagi | A61B 18/1492 606/41 |
| 6,048,349 A | 4/2000 | Winston et al. | |
| 6,053,870 A | 4/2000 | Fulton, III | |
| 6,053,904 A | 4/2000 | Scribner et al. | |
| 6,056,747 A | 5/2000 | Saadat et al. | |
| 6,063,093 A | 5/2000 | Winston et al. | |
| 6,093,185 A | 7/2000 | Ellis et al. | |
| 6,106,515 A | 8/2000 | Winston et al. | |
| 6,106,520 A | 8/2000 | Laufer et al. | |
| 6,117,131 A | 9/2000 | Taylor | |
| 6,142,992 A | 11/2000 | Cheng et al. | |
| 6,146,380 A | 11/2000 | Racz et al. | |
| 6,155,264 A | 12/2000 | Ressemann et al. | |
| 6,156,031 A | 12/2000 | Aita et al. | |
| 6,171,305 B1 | 1/2001 | Sherman | |
| 6,179,824 B1 | 1/2001 | Eggers et al. | |
| 6,193,676 B1 | 2/2001 | Winston et al. | |
| 6,193,715 B1 | 2/2001 | Wrublewski et al. | |
| 6,210,408 B1 | 4/2001 | Chandrasekaran et al. | |
| 6,217,575 B1 | 4/2001 | DeVore et al. | |
| 6,221,061 B1 | 4/2001 | Engelson et al. | |
| 6,228,076 B1 | 5/2001 | Winston et al. | |
| 6,245,054 B1 | 6/2001 | Fuimaono et al. | |
| 6,267,758 B1 | 7/2001 | Daw et al. | |
| 6,283,983 B1 | 9/2001 | Makower et al. | |
| 6,292,678 B1 | 9/2001 | Hall et al. | |
| 6,293,945 B1 | 9/2001 | Parins et al. | |
| 6,296,615 B1 | 10/2001 | Brockway et al. | |
| 6,296,636 B1 | 10/2001 | Cheng et al. | |
| 6,302,898 B1 | 10/2001 | Edwards et al. | |
| 6,304,769 B1 | 10/2001 | Arenson et al. | |
| 6,315,777 B1 | 11/2001 | Comben | |
| 6,328,699 B1 | 12/2001 | Eigler et al. | |
| 6,360,128 B2 | 3/2002 | Kordis et al. | |
| 6,364,877 B1 | 4/2002 | Goble et al. | |
| 6,385,472 B1 | 5/2002 | Hall et al. | |
| 6,394,976 B1 | 5/2002 | Winston et al. | |
| 6,395,002 B1 | 5/2002 | Ellman et al. | |
| 6,419,674 B1 | 7/2002 | Bowser et al. | |
| 6,428,551 B1 | 8/2002 | Hall et al. | |
| 6,450,989 B2 | 9/2002 | Dubrul et al. | |
| 6,475,214 B1 | 11/2002 | Moaddeb | |
| 6,485,485 B1 | 11/2002 | Winston et al. | |
| 6,508,754 B1 | 1/2003 | Liprie et al. | |
| 6,524,303 B1 | 2/2003 | Garibaldi | |
| 6,530,923 B1 | 3/2003 | Dubrul et al. | |
| 6,554,827 B2 | 4/2003 | Chandrasekaran et al. | |
| 6,562,031 B2 | 5/2003 | Chandrasekaran et al. | |
| 6,562,049 B1 | 5/2003 | Norlander et al. | |
| 6,565,562 B1 * | 5/2003 | Shah | A61B 18/1492 606/41 |
| 6,607,529 B1 | 8/2003 | Jones et al. | |
| 6,632,222 B1 | 10/2003 | Edwards et al. | |
| 6,639,999 B1 | 10/2003 | Cookingham et al. | |

(56) References Cited

U.S. PATENT DOCUMENTS

| | | |
|---|---|---|
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,896,872 B2 * | 3/2011 | Finch ................ A61B 18/1482 606/41 |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 9,179,932 B2 * | 11/2015 | Davies ............... A61B 17/3478 |
| 9,504,398 B2 * | 11/2016 | Krishnan ............ A61B 5/1076 |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0100561 A1 * | 4/2014 | Biadillah ........... A61B 18/1492 606/33 |
| 2014/0206987 A1 | 7/2014 | Urbanski et al. |
| 2014/0296769 A1 | 10/2014 | Hyde et al. |

(56) References Cited

U.S. PATENT DOCUMENTS

| | | | |
|---|---|---|---|
| 2016/0058504 A1* | 3/2016 | Davies | A61B 8/4494 |
| | | | 600/424 |
| 2016/0220741 A1 | 8/2016 | Garrison et al. | |
| 2019/0021763 A1 | 1/2019 | Zhou et al. | |
| 2019/0247035 A1 | 8/2019 | Gittard et al. | |

* cited by examiner

SYSTEM OF MEDICAL DEVICES AND METHOD FOR PERICARDIAL PUNCTURE

FIELD

This document relates to medical devices. More specifically, this document relates to systems of medical devices that can be used in pericardial puncture, and related methods.

SUMMARY

The following summary is intended to introduce the reader to various aspects of the detailed description, but not to define or delimit any invention.

Systems for pericardial puncture are disclosed. According to some aspects, a system for pericardial puncture includes a medical device having an elongate shaft extending between a proximal end and a distal end, and having an electrode at the distal end of the shaft. An impedance meter is electrically connectable with the electrode for measuring an impedance associated with the electrode. A display is provided for displaying an indication of a position of the medical device. The indication of the position is based on of the impedance.

In some examples, the indication of the position of the medical device is an indication of whether the medical device is in contact with a target tissue.

In some examples, the medical device is an introducer and the shaft has a lumen extending therethrough from the proximal end to the distal end. The shaft can include a metallic tube and an electrically insulative sheathing on the tube. The electrode can include an electrically exposed section of the tube. The shaft can include an electrical conductor extending proximally from the electrode for electrically connecting the electrode to the impedance meter.

In some examples, the system further includes a puncture device advanceable through the lumen from the proximal end to the distal end. The puncture device can be a radiofrequency puncture device and the system can further include a radiofrequency generator electrically connectable with the electrode for delivering radiofrequency energy to the electrode.

In some examples, the medical device is a puncture device. The system can further include a radiofrequency generator electrically connectable with the electrode for delivering radiofrequency energy from the electrode to puncture tissue. Alternatively, the puncture device can include a sharp tip.

Methods for pericardial puncture are also disclosed. According to some aspects, a method for pericardial puncture includes: a. advancing an introducer towards a pericardium; b. advancing a puncture device through the introducer towards the pericardium; c. puncturing the pericardium with the puncture device; and d. during at least one of step a., step b., and step c., measuring an impedance to assess a position of the introducer and/or a position of the puncture device.

In some examples, step d. is carried out during step a., and the impedance is an impedance associated with an electrode at a distal end of the introducer. In step d., the position of the distal end of the introducer can be assessed. Step d. can include determining whether the distal end of the introducer is in contact with the pericardium.

In some examples, step d. is carried out during step c., and the impedance is an impedance associated with a puncturing tip of the puncture device. In step d., the position of the puncturing tip of the puncture device can be assessed. Step d. can include determining whether the puncturing tip has punctured the pericardium.

In some examples, the method further includes: e. displaying an indication of the position of the introducer and/or the position of the puncture device. Step e. can include displaying an indication of whether the introducer has contacted the pericardium. Step e. can include displaying an indication of whether the puncture device has punctured the pericardium.

BRIEF DESCRIPTION OF THE DRAWINGS

The accompanying drawings are for illustrating examples of articles, methods, and apparatuses of the present disclosure and are not intended to be limiting. In the drawings.

DETAILED DESCRIPTION

Figure 1:
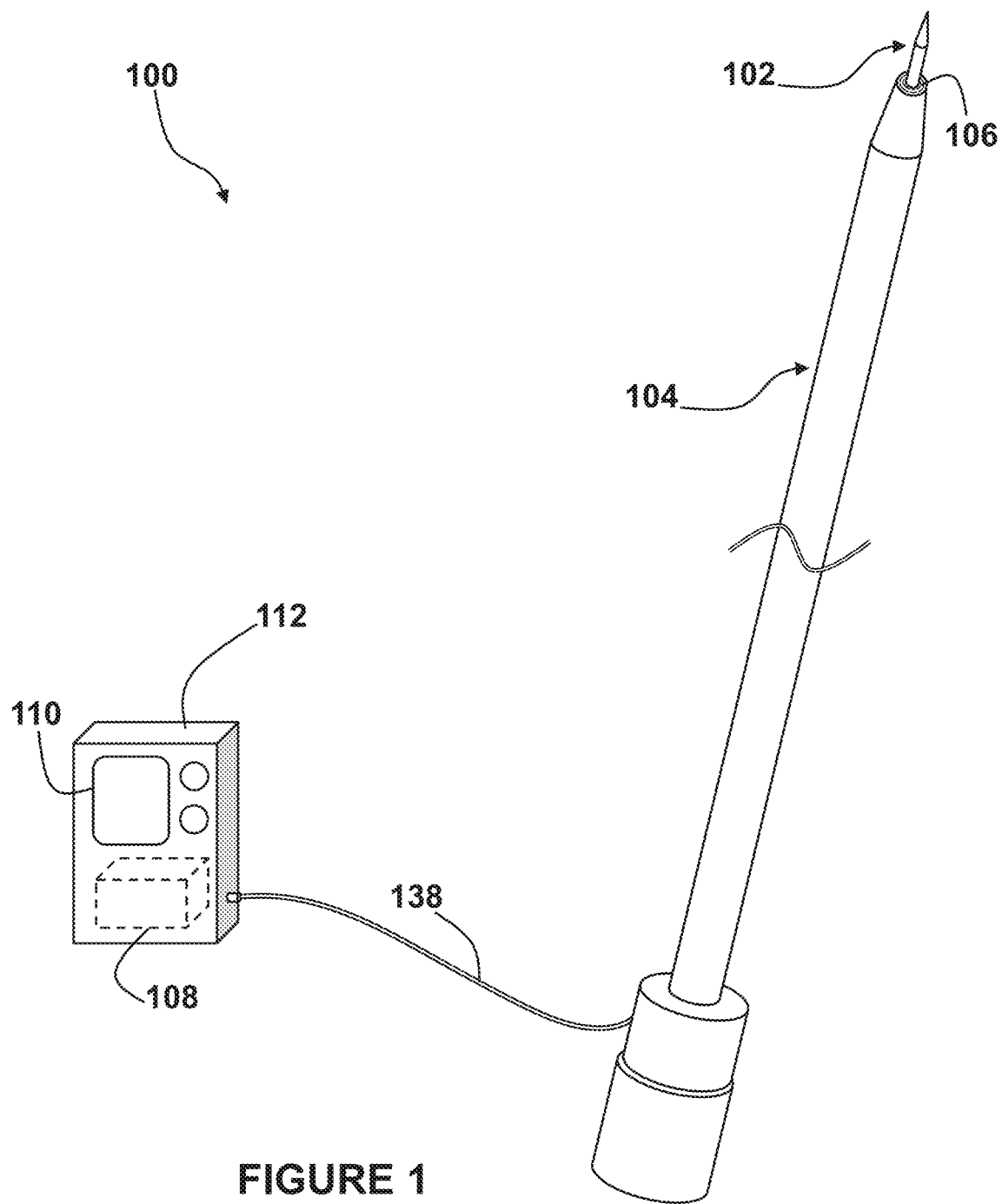
FIG. 1 is a perspective view of an example system of medical devices in an assembled state.

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein is a system that can be used in pericardial puncture procedures. The system is configured to provide an indication of a position of a medical device of the system, and more particularly, to provide an indication that a medical device of the system is in contact with a target tissue (e.g. the pericardium of the heart) or has punctured the target tissue. For example, the system can include an introducer that is percutaneously advanced towards the heart, and the system can provide an indication of whether the distal end of the introducer is in contact with the heart (and thus advancement can be stopped). In order to provide an indication of the position of the medical device, the medical device can include an electrode that is positioned to contact or approach the heart. The system can further include an impedance meter for measuring an impedance associated with the electrode (i.e. for measuring the impedance of an electrical circuit of which the electrode is a part). As the medical device is advanced towards the heart, the impedance can be monitored. When the electrode contacts or approaches the heart, the impedance will change, and this change can provide an indication that the medical device is in contact with the heart. The system can further include a display connected to the impedance meter for displaying an indication of the position of the introducer. For example, based on the impedance measured by the impedance meter, the display can be a visual display that displays text or symbols to indicate that the medical device is in contact with the heart, or an auditory display that generates a sound to indicate that the medical device is in contact with the heart. In an alternative example, the system can include a puncture device that is advanced towards the heart through an introducer and then is used to puncture the pericardium, and the system can provide an indication of whether the distal end of the puncture device is in contact with the heart or whether the distal end of the puncture device has passed through the pericardium (and thus advancement can be stopped).

Referring now to FIG. 1, an example system 100 of medical devices is shown. The system 100 generally includes a pair of medical devices, namely a puncture device 102 and an introducer 104. The puncture device 102 is receivable in and advanceable through the introducer 104. The introducer 104 can serve to atraumatically guide the puncture device 102 towards a target location in a patient's body (e.g. the heart), and the puncture device 102 can then puncture a target tissue at the target location (e.g. puncture the pericardium). As will be described in further detail below, the introducer 104 includes an electrode 106, and the system further includes an impedance meter 108 (shown in dotted line in FIG. 1) that is electrically connectable with the electrode 106 for measuring an impedance associated with the electrode 106. The impedance meter 108 can be any device that measures impedance, for example an ohm-meter or an LCR meter. The system 100 further includes a display 110 for displaying an indication of a position of the introducer 104 based on of the impedance measured by the impedance meter 108. In the example shown, the impedance meter 108 and display 110 are part of a single unit 112 (e.g. a single handheld or desktop unit).

Figure 2:
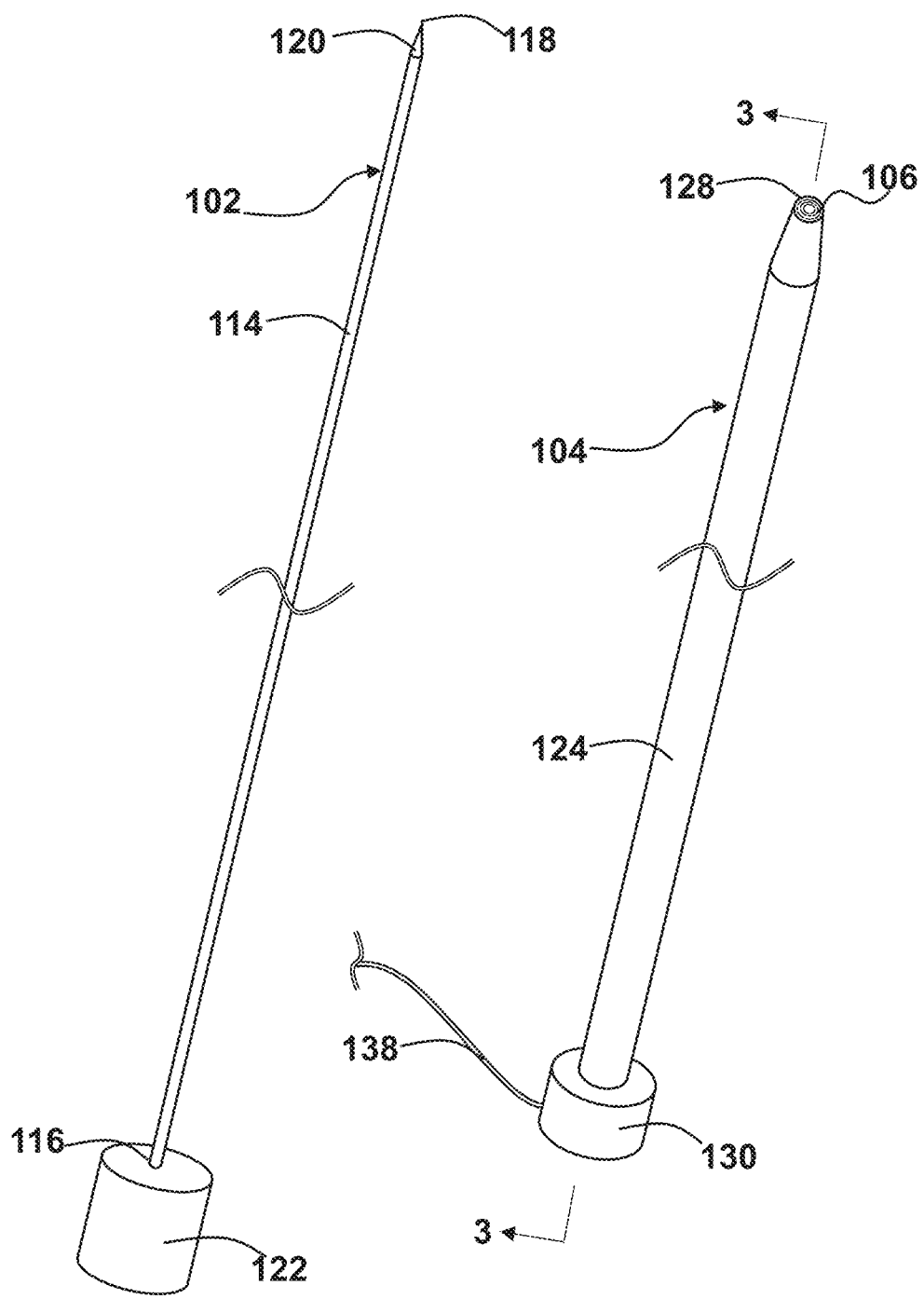
FIG. 2 is a perspective view of the puncture device and introducer of the system of FIG. 1, in an unassembled state.

Referring now to FIG. 2, in the example shown, the puncture device 102 is a mechanical puncture device, and includes elongate shaft 114 (also referred to herein as a "puncture device shaft") extending between a proximal end 116 (also referred to herein as a "puncture device proximal end") and a distal end 118 (also referred to herein as a "puncture device distal end"). A puncturing tip 120 is at the distal end, for puncturing tissue. In the example shown, the puncturing tip 120 is a sharp tip. The sharp tip can be, for example, beveled, pyramidal, or conical (as shown). A hub 122 (also referred to herein as a "puncture device hub") is at the proximal end 116, for handling and manipulating the puncture device 102.

In alternative examples, the puncture device can be a radiofrequency (RF) puncture device. In such examples, the puncturing tip can include an RF puncture electrode, and the system can include an RF generator to which the RF puncture electrode is electrically connectable for the delivery of RF energy to the RF puncture electrode. In such examples, the distal end of the puncture device can be blunt.

Referring still to FIG. 2, in the example shown, the introducer 104 includes elongate shaft 124 (also referred to herein as an "introducer shaft") extending between a proximal end 126 (shown in FIG. 3, and also referred to herein as an "introducer proximal end") and a distal end 128 (also referred to herein as an "introducer distal end"). The distal end 128 of the shaft 104 is generally blunt, in order to avoid damaging tissue. A hub 130 (also referred to herein as an "introducer hub") is at the proximal end 126 of the shaft 124, for handling and manipulating the introducer 104.

Figure 3:
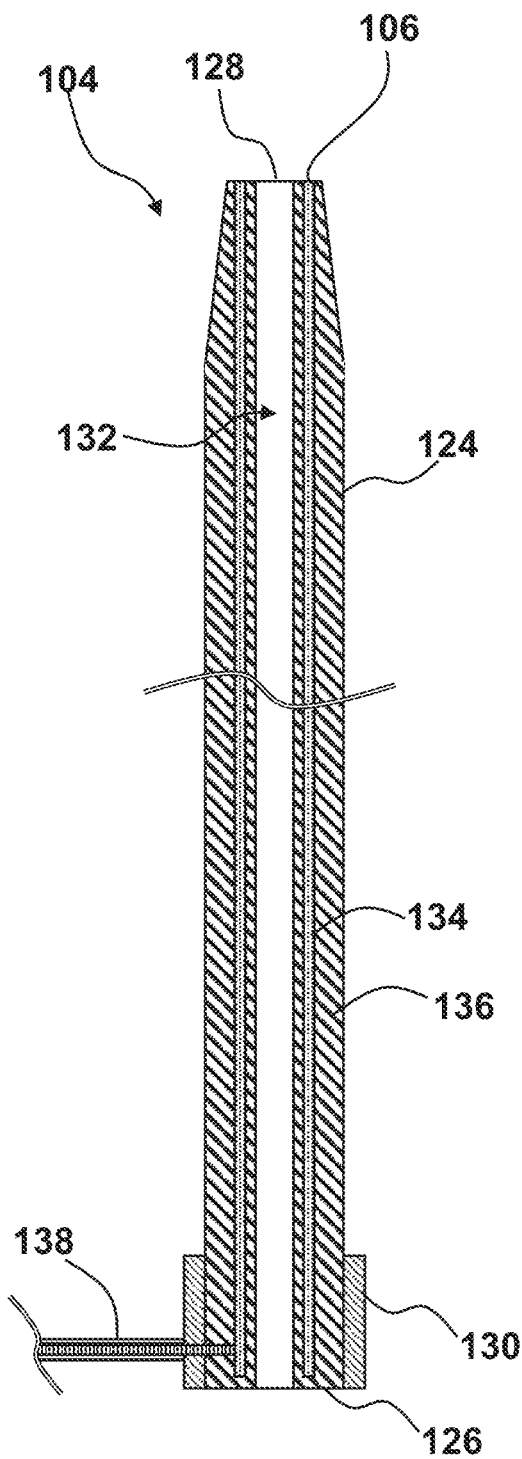
FIG. 3 is a cross-section taken along line 3-3 in FIG. 2.
Figure 4:
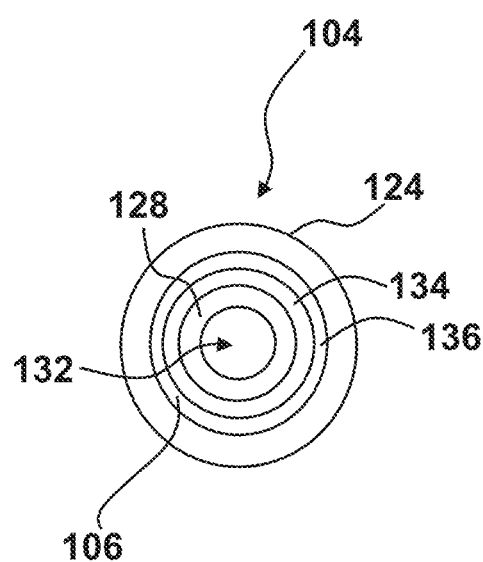
FIG. 4 is an end view of the introducer of FIG. 2.

Referring to FIGS. 3 and 4, the introducer 104 includes a lumen 132 extending therethrough, from the proximal end 126 of the shaft 124 to the distal end 128 of the shaft 124. The puncture device 102 (not shown in FIGS. 3 and 4) is advanceable through the lumen 132, from the proximal end 126 of the shaft 124 to the distal end 128 of the shaft 124, to position the puncturing tip 120 of the puncture device 102 proud of the distal end 128 of the shaft 124.

Referring still to FIGS. 3 and 4, as mentioned above, the introducer includes an electrode 106, which is at the distal end 128 of the shaft 124 and is distally facing. More specifically, in the example shown, the shaft 124 includes an electrically conductive tube 134 (e.g. a steel tube or other metallic tube), and an electrically insulative sheathing 136 (e.g. a high-density polyethylene sheathing or other polymeric sheathing) on the tube 134. At the distal end 128, the tube 134 is electrically exposed, and the electrically exposed section of the tube 134 forms the electrode 106. The remainder of the tube 134 provides an electrical conductor that extends proximally from the electrode 106, for electrically connecting the electrode 106 to the impedance meter 108, via an insulated wire 138.

In alternative examples, the electrode can be of another configuration. For example, the electrode can be a stand-alone metallic element at or near the distal end of the shaft, and a wire or other electrical conductor can extend proximally from the electrode for connecting the electrode to the impedance meter.

Figure 5:
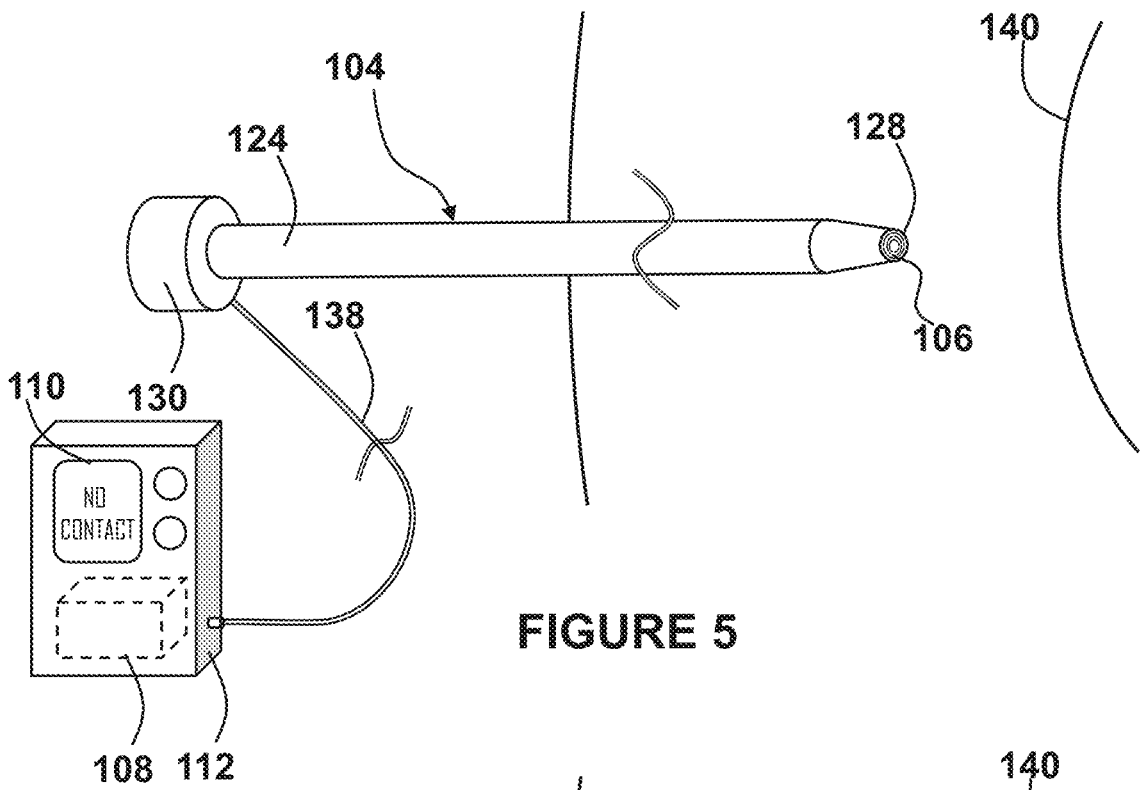
FIG. 5 is a schematic drawing showing a step of a method for pericardial puncture.
Figure 6:
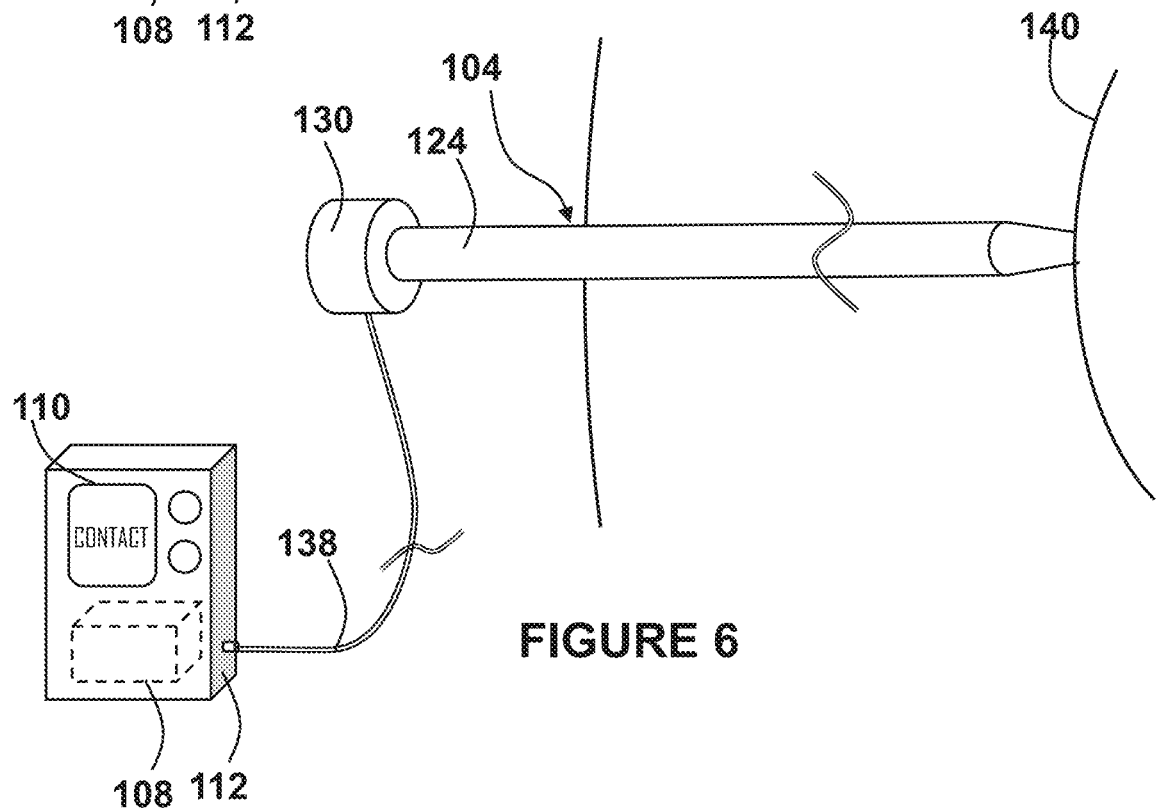
FIG. 6 is a schematic drawing showing a step subsequent to that of FIG. 5.

Referring now to FIGS. 5 and 6, in use, the introducer 104 can be advanced percutaneously towards the pericardium 140 of the heart. For example, the introducer 104 can be advanced via the subxiphoid approach, with the puncture device (not shown in FIGS. 5 and 6) shrouded within the lumen 132 (not visible in FIGS. 5 and 6) in order to prevent tissue coring, or extending slightly proud of the introducer to facilitate passage through adipose tissue. As the introducer 104 is advanced, the impedance associated with the electrode 106 (i.e. the impedance of an electrical circuit of which the electrode 106 is a part) can be measured by the impedance meter 108, to assess the position of the introducer 104. More specifically, referring first to FIG. 5, as the introducer 104 is advanced, the impedance meter 108 can continuously measure the impedance associated with the electrode 106. When the electrode 106 (not visible in FIG. 6) contacts the pericardium 140 of the heart, as shown in FIG. 6, the impedance will change, and this change can be used as an indication of the position of the electrode 106 relative to the pericardium, which can in turn be used as an indication of the position of the distal end 128 of the introducer 104. As the introducer 104 is advanced, the impedance meter 108 can communicate with the display 110, and based on the impedance, the display 110 can display an indication of the position of the introducer 104. For example, as shown in FIGS. 5 and 6, the display 110 can display an indication of whether or not the electrode 106 is in contact with the pericardium 140 of the heart. This can be done by displaying text, or by a change in color, or by illumination or a light, or by the emission of a sound. Alternatively, the display 110 can display raw impedance measurements, which can then be interpreted by a user in order to determine whether or not the electrode 106 is in contact with the pericardium 140 of the heart.

When the display 110 indicates that the introducer 104 is in contact with the heart, the method can proceed. That is, the puncture device 102 can be advanced out of the lumen 132, to puncture the pericardium.

In an alternative example (not shown), the electrode can be on the puncture device. For example, in the case of a mechanical puncture device, the electrode can be part of the puncturing tip. In the case of an RF puncture device, the RF electrode can also serve as the electrode for impedance measurement. The system can then measure impedance to assess the position of the puncture device. More specifically, as the puncture device passes through the pericardium, the impedance associated with the electrode will change and can be measured to assess the position of the puncturing tip, to determine whether the puncturing tip has punctured the pericardium. The display can then display an indication of whether the puncture device has punctured the pericardium.

As mentioned above, in the example shown, the impedance meter and display are part of a single unit. In alternative examples, the impedance meter and display may be provided in separate units. For example, the impedance meter can be built into the hub of the introducer, and the display can be provided as a standalone display.

In any of the above examples, the puncture device and/or the introducer can include one or more radiopaque markers, to facilitate viewing under fluoroscopy.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A system for pericardial puncture comprising:
   a medical assembly comprising,
   an introducer having an elongate shaft extending between a proximal end and a distal end and defining a single lumen therethrough, the elongate shaft having a longitudinal axis extending between the proximal end and the distal end, the elongate shaft comprising:
   an electrically conductive metallic tube;
   a polymeric, electrically insulative sheathing on the metallic tube, the insulative sheathing having a tapered portion surrounding a distal portion of the electrically conductive metallic tube;
   the introducer having a distally facing electrode at the distal end of the shaft, the electrode comprising a distal end portion of the metallic tube that is electrically exposed through the polymeric insulative sheathing, the electrode encircling the lumen and being coaxial with the longitudinal axis of the elongate shaft, and
   an elongated puncture device disposed within the lumen and extendable from the distal end of the shaft;
   an impedance meter electrically connectable with the electrode for measuring an impedance associated with the electrode; and
   a display for displaying an indication of a position of the medical assembly device, wherein the indication of the position is based on of the impedance.

2. The system of claim 1, wherein the indication of the position of the medical assembly is an indication of whether the medical is in contact with a target tissue.

3. The system of claim 1, wherein the shaft comprises an electrical conductor extending proximally from the electrode for electrically connecting the electrode to the impedance meter.

4. The system of claim 1, wherein
   the puncture device is a radiofrequency puncture device; and
   the system further comprises a radiofrequency generator electrically connectable with the electrode for delivering radiofrequency energy to the electrode.

5. The system of claim 1, wherein the puncture device comprises a sharp tip.

6. The system of claim 1, wherein the indication of a position of the medical assembly device includes an indication of whether or not the electrode is in contact with a pericardium of the heart.

7. The system of claim 6, wherein the indication of whether or not the electrode is in contact with the pericardium of the heart is displayed text.

8. A method for pericardial puncture, comprising:
   a. advancing an introducer towards a pericardium, the introducer having a distal end with a distalmost tip, the introducer having an elongate shaft, the elongate shaft having a longitudinal axis extending between the proximal end and the distal end, the elongate shaft comprising: an electrically conductive metallic tube; a polymeric, electrically insulative sheathing on the metallic tube, the insulative sheathing having a tapered portion surrounding a distal portion of the electrically conductive metallic tube; the introducer including a distally facing electrode at the distalmost tip, the electrode comprising a distal end portion of the metallic tube that is electrically exposed through the polymeric insulative sheathing, and the electrode being coaxial with the longitudinal axis of the elongate shaft;
   b. advancing a puncture device through the introducer towards the pericardium, the puncture device including a puncturing tip having a puncturing tip electrode;
   c. puncturing the pericardium with the puncture device; and
   d. during at least one of step a., step b., and step c., measuring an impedance to assess a position of the introducer and a position of the puncture device, the impedance associated with the distally facing electrode and the puncturing tip electrode.

9. The method of claim 8, wherein in step d., the position of the distal end of the introducer is assessed.

10. The method of claim 8, wherein step d. comprises determining whether the distal end of the introducer is in contact with the pericardium.

11. The method of claim 8, wherein step d. comprises determining whether the puncturing tip has punctured the pericardium.

12. The method of claim 8, further comprising:
    e. displaying an indication of the position of the introducer and/or the position of the puncture device.

13. The method of claim 12, wherein step e. comprises displaying an indication of whether the introducer has contacted the pericardium, wherein the indication includes text, illumination, or light.

14. The method of claim 12, wherein step e. comprises displaying an indication of whether the puncture device has punctured the pericardium, wherein the indication includes text, illumination, or light.

\* \* \* \* \*